United States Patent
Brown et al.

(10) Patent No.: US 7,331,986 B2
(45) Date of Patent: Feb. 19, 2008

(54) INTRALUMINAL MEDICAL DEVICE HAVING IMPROVED VISIBILITY

(75) Inventors: Brian Brown, Hanover, MN (US); Paul Chouinard, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 178 days.

(21) Appl. No.: 10/269,112

(22) Filed: Oct. 9, 2002

(65) Prior Publication Data

US 2004/0073291 A1  Apr. 15, 2004

(51) Int. Cl.
A61F 2/06 (2006.01)

(52) U.S. Cl. ..................................... 623/1.15
(58) Field of Classification Search ............... 623/1.15, 623/1.34
See application file for complete search history.

(56) References Cited

U.S. PATENT DOCUMENTS

| | | | |
|---|---|---|---|
| 5,741,327 A | 4/1998 | Frantzen | 623/1 |
| 5,755,770 A | 5/1998 | Ravenscroft | 623/1 |
| 5,824,046 A | 10/1998 | Smith et al. | 623/1 |
| 5,858,556 A | 1/1999 | Eckert et al. | 428/586 |
| 5,861,027 A | 1/1999 | Trapp | 623/1 |
| 5,922,020 A | 7/1999 | Klein et al. | 623/1 |
| 6,013,854 A * | 1/2000 | Moriuchi | 623/1.11 |
| 6,022,374 A | 2/2000 | Imran | 623/1 |
| 6,231,598 B1 | 5/2001 | Berry et al. | 623/1.15 |
| 6,272,370 B1 | 8/2001 | Gillies et al. | 600/411 |
| 6,280,385 B1 | 8/2001 | Melzer et al. | 600/423 |
| 6,293,966 B1 * | 9/2001 | Frantzen | 623/1.15 |
| 6,299,635 B1 * | 10/2001 | Frantzen | 623/1.17 |
| 6,331,188 B1 | 12/2001 | Lau et al. | 623/1.13 |
| 6,334,871 B1 | 1/2002 | Dor et al. | 623/1.34 |
| 6,340,366 B2 | 1/2002 | Wijay | 623/1.13 |
| 6,340,367 B1 | 1/2002 | Stinson et al. | 623/1.34 |
| 6,355,058 B1 | 3/2002 | Pacetti et al. | 623/1.15 |
| 6,361,557 B1 | 3/2002 | Gittings et al. | 623/1.13 |
| 6,361,759 B1 | 3/2002 | Frayne et al. | 424/9.323 |
| 6,379,381 B1 | 4/2002 | Hossainy et al. | 623/1.42 |
| 6,402,777 B1 | 6/2002 | Globerman et al. | 623/1.11 |
| 6,524,335 B1 | 2/2003 | Hartley et al. | 623/1.13 |
| 6,656,215 B1 | 12/2003 | Yanez et al. | 623/1.13 |
| 2001/0029397 A1 | 10/2001 | Thompson | 623/1.16 |
| 2002/0007212 A1 | 1/2002 | Brown et al. | 623/1.16 |
| 2002/0022876 A1 | 2/2002 | Richter et al. | 623/1.15 |
| 2002/0120322 A1 | 8/2002 | Thompson et al. | 623/1.11 |
| 2003/0176914 A1 | 9/2003 | Rabkin et al. | 623/1.15 |
| 2004/0111147 A1 | 6/2004 | Rabkin et al. | 623/1.15 |

FOREIGN PATENT DOCUMENTS

| | | |
|---|---|---|
| EP | 0801933 A1 | 10/1997 |
| WO | 9925273 | 5/1999 |
| WO | 0132099 | 10/2000 |
| WO | 0158386 | 8/2001 |

* cited by examiner

*Primary Examiner*—Corrine McDermott
*Assistant Examiner*—Christopher Prone
(74) *Attorney, Agent, or Firm*—Vidas, Arrett & Steinkraus, PA (57) ABSTRACT

A stent may be formed of at least one structural material having a pattern including at least one serpentine structure, which extends about the longitudinal axis of the stent. The structure is formed of a plurality of struts. Adjacent struts are interconnected by end portions having inner turns and outer turns. At least some of the end portions are elongated and other end portions are non-elongated and have a predetermined length. At least one of said elongated end portions is configured to serve as a fiducial marker.

32 Claims, 4 Drawing Sheets

INTRALUMINAL MEDICAL DEVICE HAVING IMPROVED VISIBILITY

BACKGROUND OF THE INVENTION

Stents are generally tubular shaped devices that function to hold open a segment of a blood vessel or other anatomical lumen and are useful in the treatment of atherosclerotic stenoses in blood vessels. Stents are particularly suitable for use in supporting and holding back a dissected arterial lining that can occlude the fluid passageway there through.

Stents are available in a variety of configurations, including self-expanding and mechanical expanding varieties, but regardless of the configuration, are typically delivered to the site of the atherosclerotic stenosis through the use of a catheter delivery device.

To accomplish precise placement of stents, various means are employed for identifying the position of the stent within a blood vessel. As the stents themselves are typically formed of a metal, metal alloy or polymeric material which is not readily visible using known techniques for viewing the stent such as fluoroscopy or MRI, such characteristics must be imparted to the stent structure. One method is to impart radiopacity to the stent structure such as by attachment of markers to the stent structure, or by making the entire stent from a radiopaque material, so that, through the use of fluoroscopy, the position of the stent within a blood vessel can be identified. Once the stent with its radiopaque markers has been implanted, identification of the stent position during subsequent checkups of the treated segment is easily accomplished because the markers remain visible under fluoroscopy. Another method is to provide stent materials which are visible using MRI.

Stents are most commonly formed of materials which have little radiopacity such as stainless steel or shape memory metal alloys such as NITINOL® which is a nickel-titanium shape memory alloy, for example. For one, making the entire stent out of a radiopaque material can be quite costly. Another disadvantage is that the stent may fluoresce too brightly which may actually make it more difficult for the physician to accurately position the stent, as well as to make follow up checks on the functioning of the stent more difficult.

There have been several methods employed for attaching radiopaque markers to a stent. One method has been to coat the deformable portions of the stent with radiopaque material. This can require a relatively thick coating in order to provide enough radiopaque material to be visible using fluoroscopy, and can also alter the mechanical performance of the stent.

Another method has been to insert radiopaque material into a hollow stent wire.

Other methods of attaching radiopaque markers have been employed such as that described in U.S. Pat. No. 6,334,871 in which radiopaque markers described therein as rivets are inserted into openings in the stent.

There remains a need in the art for improved stents as well as other improved intraluminal medical devices which are easily and readily visualized in the vasculature of a patient for accurate placement and for accurate future detection in the desired body lumen, and to improved methods of making the same.

All U.S. patents and applications and all other published documents mentioned anywhere in this application are incorporated herein by reference in their entirety.

SUMMARY OF THE INVENTION

The present invention relates to intraluminal medical devices, including stents and stent grafts having fiducial markers to enhance visibility of the device in the vasculature of a patient both during the delivery and placement of the device, and for future observation of the device during follow up visits.

In general, the stents of the present invention are tubular structures formed of a serpentine structure that typically includes at least one serpentine band and desirably a plurality of serpentine bands which are interconnected by connecting members between adjacent serpentine bands. The serpentine bands may be in the form of circumferential bands or bands which spiral about the longitudinal axis of the stent. The serpentine bands are formed of a plurality of struts, adjacent ones of which are connected by alternating end portions. The end portions have inner turns and outer turns. Some of the end portions in the stent circular band pattern are elongated and are configured so as to provide enhanced visibility of that portion of the stent structure. The elongated end portions do not extend substantially beyond the non-elongated end portions, however. The outer turns of the elongated portions do not have to align longitudinally with the outer turns of the non-elongated portions, and the inner turns of the elongated portions do not have to align longitudinally with the inner turns of the non-elongated portions.

In some embodiments, the enhanced visibility is provided by having elongated end portions with increased mass. The elongated end portions may also be enlarged in addition to being elongated. The elongated end portions with higher mass are preferentially configured such that the elongated end portions do not extend substantially longitudinally beyond the other non-elongated end portions of the band.

In one embodiment, the end portion includes an extension which incorporates a fiducial marker. In this embodiment, the overall length of the extension and the end portion, does not extend substantially beyond the length of the other end portions which are neither elongated, nor have any extensions. In this embodiment the outer turns of the end portions having the extension do not have to longitudinally align with the outer turns of the other end portions, and the inner turns of the end portions having the extensions do not have to longitudinally align with the inner turns of the other end portions.

In another embodiment, the elongated end portions may be adapted to receive a fiducial marker such as a plug, rivet, wire winding, band, filling, coating or the like.

DETAILED DESCRIPTION OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

Structures which are in longitudinal alignment or which are aligned longitudinally, for the purposes of this disclosure, are structure which are at the same axial position along the longitudinal axis of the stent but which may be located apart from one another about the circumference of the stent. Thus, for example, in the stents of FIGS. 6 and 7, proximal-most outer turns 20a and 20b are substantially longitudinally aligned with one another and distal-most outer turns 20a and 20b are substantially longitudinally aligned with one another.

In general, the stents of the present invention are tubular structures formed of a serpentine structure that typically includes at least one and desirably a plurality of serpentine bands. The serpentine bands may be circumferential bands or may spiral about the longitudinal axis of the stent. Each serpentine band is formed of a plurality of struts which are interconnected by end portions, each end portion having an inner turn and an outer turn. Where a plurality of serpentine bands are present, the serpentine bands are also interconnected by connecting elements. Some of the end portions of the stent structures of the present invention are adapted to provide enhanced visibility using imaging techniques such as fluoroscopy or magnetic resonance imaging (MRI) by providing elongated or extended end portions of sufficient area or mass which can serve as fiducial markers themselves or in conjunction with at least a second material provided in the region of the elongated or extended end portion.

As used herein, the term "fiducial marker" shall be used to include those portions of the stent which have properties which make them have locally enhanced visibility in the imaging modality which will be used to acquire an image of the patient's body. For example, where x-ray based imaging modalities will be used, the fiducial markers are of increased area or mass and/or of more radiopaque material. If magnetic resonance imaging is employed, the fiducial markers have magnetic resonance properties which are different from the magnetic resonance properties of the remainder of the stent.

Figure 1:
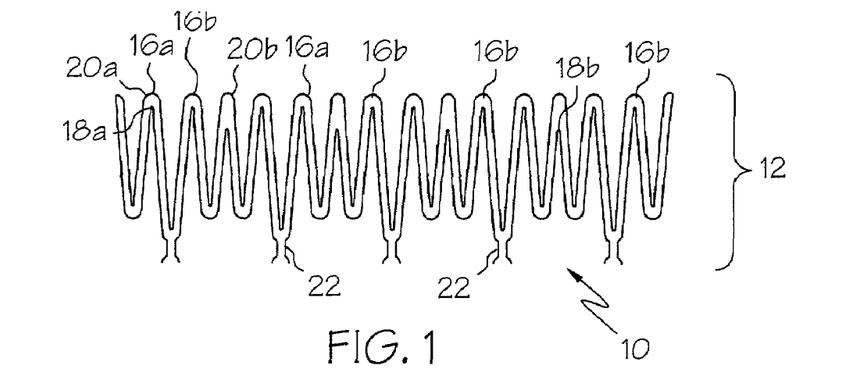
FIG. 1 is a partial view of a stent according to the present invention having elongated end portions.

Turning now to the figures, FIG. 1 is a partial view of a stent 10 formed of a plurality of circumferential bands 12 which are interconnected by connecting elements 22. The connecting elements 22 shown in this and the following figures are shown as straight connecting elements. However, other variations may be employed including, for example, curved, bent, linear, curvilinear, and so forth. Shown in FIG. 1 is a single circumferential band 12 but the connecting elements 22 to the next circumferential band are visible. Band 12 is formed of a plurality of struts interconnected by end portions 16a, 16b, each end portion having an inner turn 18a, 18b and an outer turn 20a, 20b. Some of the end portions 16b of each circumferential band are designed to exhibit enhanced visibility, desirably by providing enhanced radiopacity when using fluoroscopic techniques, or by providing different MRI properties when using MRI. In this particular embodiment, the end portions 16b have an elongated structure for providing increased mass and enhanced radiopacity.

In this embodiment, not all of the turns of the end portions need be substantially longitudinally aligned with one another. However, the elongated end portions 16b have outer turns 20b, which do not extend substantially beyond the outer turns 20a of any of the other non-elongated end portions 16a. Further, the inner turns, 18b, of the elongated end portions 16b, are not substantially longitudinally aligned with the inner turns 18a of the non-elongated end portions 16a.

Figure 2:
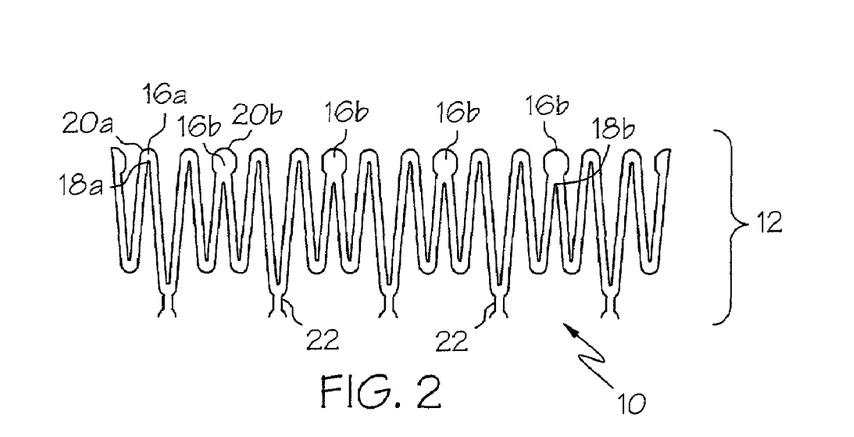
FIG. 2 is a partial view of an alternative embodiment of a stent according to the present invention having elongated and enlarged end portions.

FIG. 2 shows generally at 10, a partial view of another embodiment of a stent structure according to the present invention. In this embodiment, the overall structure is substantially similar to that of FIG. 1, but, the end portions 16b, are not only elongated, but are further enlarged as well. Again, none of the outer turns 20b, of the elongated, enlarged end portions 16b, extend longitudinally substantially beyond the end portions of 16a. The inner turns 18b of the elongated and enlarged end portions 16b, are not substantially longitudinally aligned with the inner turns 18a of the non-elongated end portions 16a.

Figure 3:
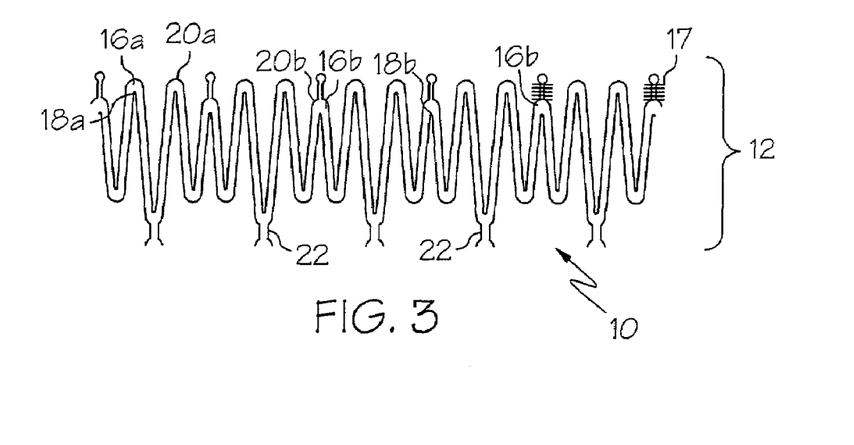
FIG. 3 is a partial view of an alternative embodiment of a stent according to the present invention having end portions designed for accepting fiducial markers for enhancing visibility.
Figure 4:
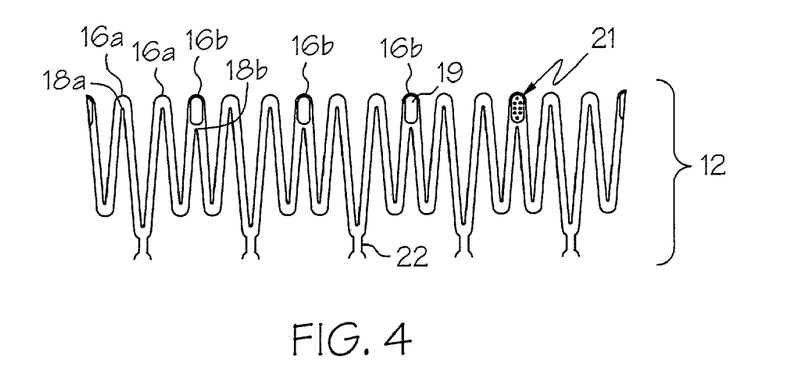
FIG. 4 is a partial view of an alternative embodiment of a stent according to the present invention in which the end portions include a void for inserting fiducial markers.
Figure 5:
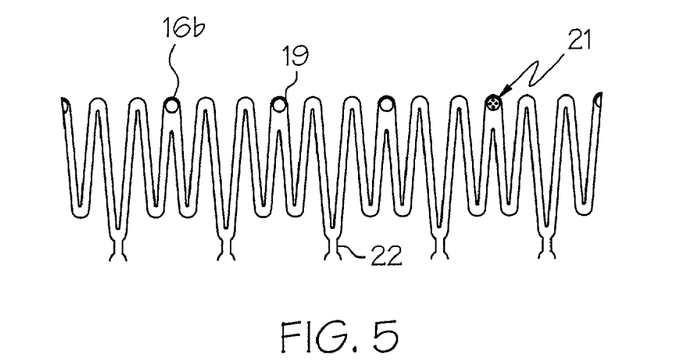
FIG. 5 is a partial view of an alternative embodiment of a stent similar to that shown in FIG. 4 wherein the end portions have alternative voids for inserting fiducial markers.

FIG. 3 is a partial view of yet another embodiment of a stent according to the present invention. In this embodiment, the end portions 16b, have an extension 17 for attaching a fiducial marker such as a wire winding, marker band, plating, coating and the like, for example. The inner turns 18b of the end portions 16b having the extensions 17 do not longitudinally align with the inner turns 18a of the end portions 16a which have no extensions. The outer turns 20b of end portions 16b which have extensions 17, are not substantially longitudinally aligned with the outer turns 20a of the other end portions 16a which do not have any extensions. The extensions 17 of the end portions 16b, do not, however, extend substantially beyond the length of the end portions 16a. FIGS. 4 and 5 are illustrative of another embodiment of the stent structure according to the present invention in which the elongated end portions are adapted for receiving some sort of fiducial marker such as a plug, rivet, filling, plating, coating and so forth.

FIG. 4 illustrates an embodiment of the present invention in which a substantial portion of the elongated end portions 16b is adapted with a fitting 19 for accepting a visibility enhancing marker 21. The circumferential band as shown has a plurality of non-elongated end portions 16a and a plurality of elongated end portions 16b. Again, the length of the elongated end portions 16b does not extend substantially beyond the length of the non-elongated end portions 16a. The outer turns 20b of the elongated end portions 16b are substantially longitudinally aligned with the outer turns 20a of the non-elongated end portions 16a in this embodiment, but this is not a requirement. The inner turns 18b of the elongated end portions 16b are not substantially longitudinally aligned with the inner turns 18a of the non-elongated end portions 16a.

FIG. 5 illustrates an embodiment of the present invention which is substantially similar to that shown in FIG. 4, with the exception that the fitting 17 for accepting the fiducial marker 19, is smaller, in relation to the elongated end portion 16b.

Figures 6, 6A:
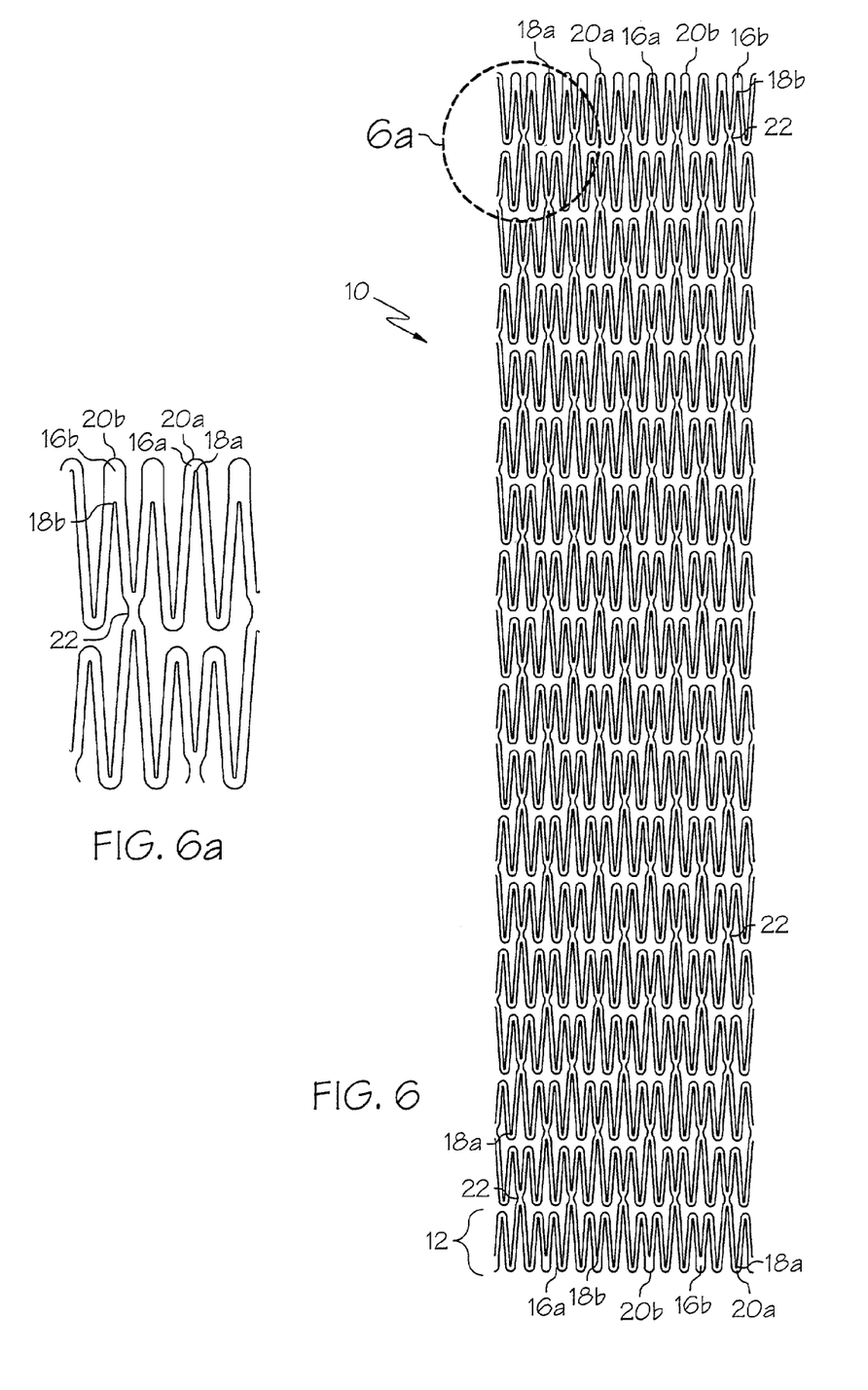
FIG. 6 is a flat pattern of a stent according to the present invention wherein the stent exhibits two elongated end portions interspersed with a non-elongated end portion.
FIG. 6a is an exploded partial view of the same stent as shown in FIG. 6.

FIG. 6 shows a flat pattern of a stent 10 according to the present invention formed of a plurality of bands 12 interconnected by connecting elements 22. The actual stent is tubular. Band 12 is formed of a plurality of struts interconnected by end portions 16a, 16b, each end portion having an inner turn 18a, 18b and an outer turn 20a, 20b. Some of the end portions 16b of each circumferential band are designed to exhibit enhanced visibility, desirably by providing enhanced radiopacity when using fluoroscopic techniques, or by providing different MRI properties when using MRI. In this particular embodiment, the end portions 16b, have an elongated structure for providing increased mass and enhanced radiopacity.

In the embodiment shown in FIG. 6, there are at least two adjacent elongated end portions 16b separated by a non-elongated end portion 16a at one end of the stent and at least two adjacent non-elongated end portions 16a separated by an elongated end portion 16b at the other end of the stent.

FIG. 6a is an exploded view of a portion of the stent 10 shown in FIG. 6 illustrating the elongated end portions 16b. Variations may be made in the structure shown in FIGS. 6 and 6a such as having more than two adjacent elongated end portions 16b, for example. Furthermore, while connecting elements 22 shown in FIGS. 6 and 6a are straight, other variations may be employed such as curved, bent, linear, curvilinear, and so forth.

Figure 7:
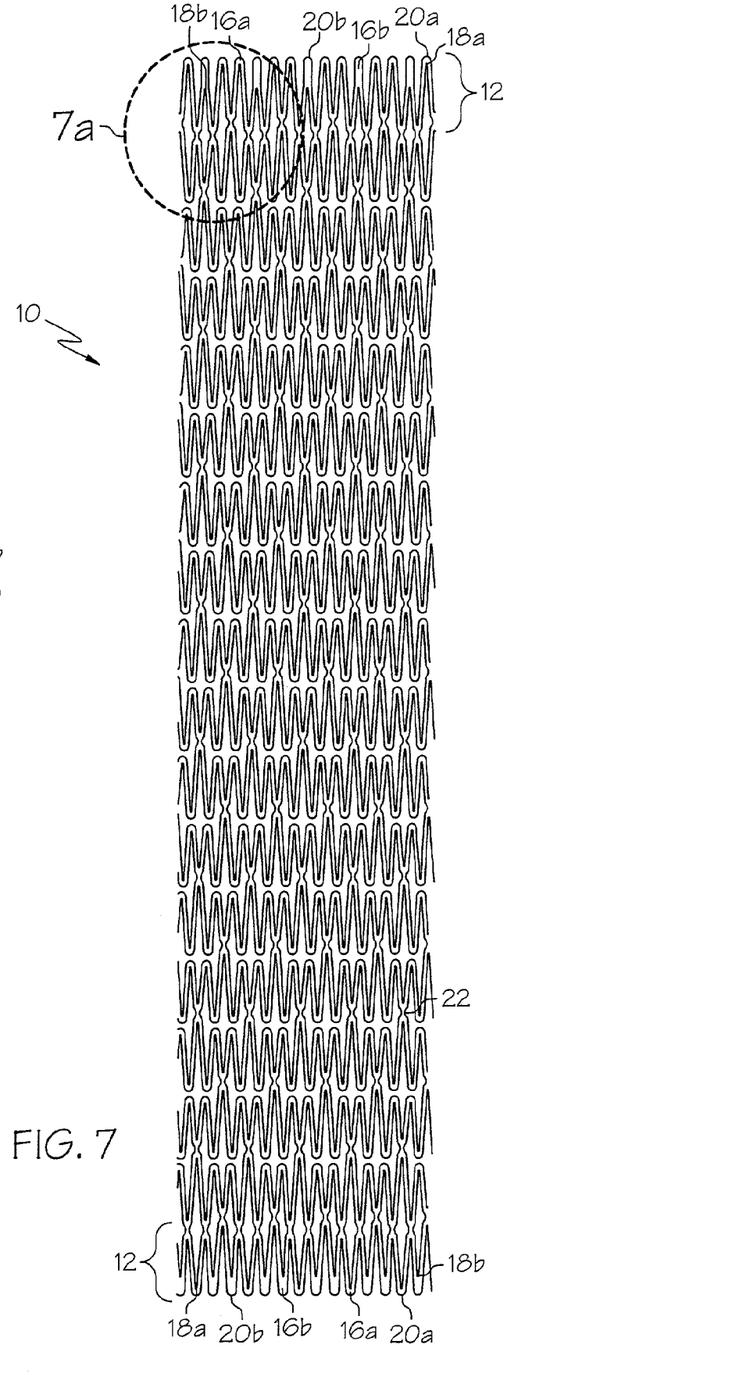
FIG. 7 is a flat pattern of a stent according to the present invention wherein the stent exhibits two non-elongated end portions separated by one elongated end portion.

FIG. 7 shows a flat pattern of an alternative embodiment of the stent 10 according to the present invention formed of a plurality of interconnecting bands 12 interconnected by connecting elements 22. The actual stent is tubular. Band 12 is formed of a plurality of struts interconnected by end portions 16a, 16b, each end portion having an inner turn 18a, 18b and an outer turn 20a, 20b. Some of the end portions 16b of each circumferential band are designed to exhibit enhanced visibility, desirably by providing enhanced radiopacity when using fluoroscopic techniques, or by providing different MRI properties when using MRI. In this particular embodiment, the end portions 16b have an elongated structure for providing increased mass and enhanced radiopacity.

Figure 7A:
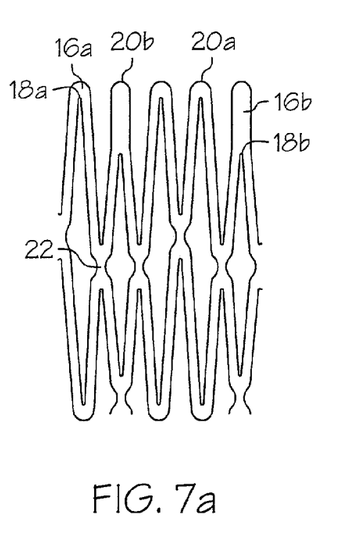
FIG. 7a is an exploded partial view of the same stent as shown in FIG. 7.

In the embodiment shown in FIG. 7, there are two adjacent non-elongated end portions 16a separated by an elongated end portion 16b at one end of the stent and there are two adjacent elongated end portions 16b separated by a non-elongated end portion 16a at the other end of the stent. FIG. 7a is an exploded view of a portion of the stent 10 shown in FIG. 7 illustrating the elongated end portions 16b. Variations may be made in the structure shown in FIGS. 7 and 7a such as having more than two adjacent non-elongated end portions 16a, for example. Furthermore, while connecting elements 22 shown in FIGS. 6 and 6a are straight, other variations may be employed such as curved, bent, linear, curvilinear, and so forth.

In accordance with the invention, a stent may comprise a single band such as that shown in FIGS. 1-7a or a plurality of such bands.

Figure 8:
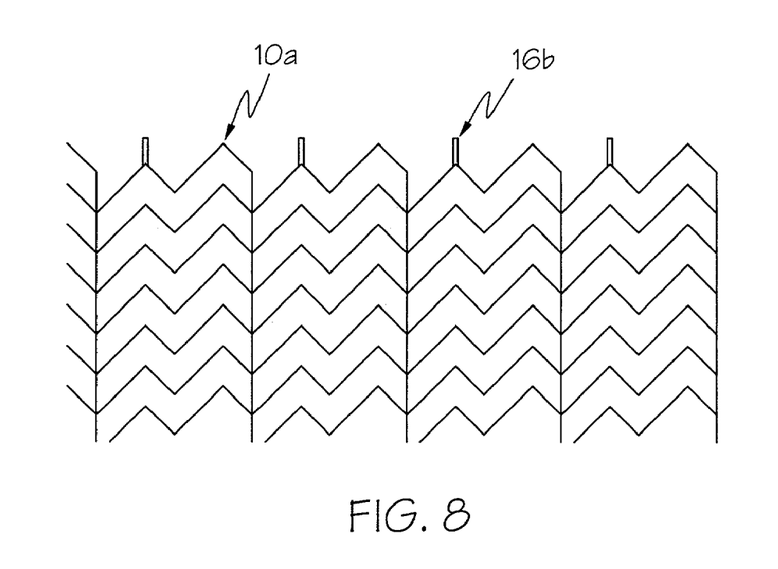
FIG. 8 is a schematic of a spiral embodiment of the stent.

The inventive stents may also be provided in other configurations as well. For example, any of the inventive stents disclosed herein may also be provided in spiral embodiments in which the serpentine bands or cellular structures spiral about the longitudinal axis of the stent. An example of such a configuration is shown schematically in a flat pattern in FIG. 8. Some of the peaks 16b at the end of the stent are provided with elongated end portions to serve as fiducial markers and some of the peaks 16a do not have elongated end portions.

Any of the inventive stents disclosed herein may also be provided in a 'jelly roll' configuration. For example, the flat pattern of FIG. 7 may be rolled into a tube without securing the longitudinal edges to one another. Such a stent would be deployed by unrolling of the stent and expansion of the cells or bands which extend about the longitudinal axis of the stent. An example of such a stent is disclosed in WO0132099.

The stents according to the present invention are formed of at least one base material hereinafter referred to as the structural material. Any suitable material known in the art for forming such intraluminal medical devices may be employed including both metallic materials and polymeric materials, although metallic materials are preferred.

Examples of suitable metallic materials include, but are not limited to stainless steel, and shape memory alloys. Examples of such materials include, but are not limited to, NITINOL® which is a nickel-titanium alloy, cobalt-chromium alloys such as ELGILOY®, platinum-tungsten alloys, and so forth. Other alloys which may be employed in making formation of the stent structure include, but are not limited to, cobalt chromium alloys, other alloys of titanium cobalt-chromium molybdenum alloys, and so forth.

The fiducial markers, as described above, enhance visibility of the stent in conjunction with an imaging modality such as, for example, MRI and fluoroscopy.

One way to provide regions of altered MR contrast in an intraluminal medical device is to employ polymeric materials containing a paramagnetic ion. Examples of coatings which are suitable for enhancing the visualization of desired regions of a stent are disclosed in U.S. Pat. No. 6,361,759, incorporated herein by reference. Ferromagnetic materials such as iron, nickel, cobalt and alloys of these materials may also enhance the visualization of the desired regions of the stent. Paramagnetic materials including gadolinium and alloys and salts thereof may also be used to alter the imaging characteristics of the stent.

Other compounds which may find utility herein and serve as key components of various contrast agents for MRI include, but are not limited to polychelating and amphiphilic polymers. Some examples of polychelating polymers are those having poly-L-lysine (PLL) as the main chain and chelating moieties such as diethylene traimine pentaacetic acid or DTPA as side groups.

It may further be noted that some polymer surfaces may optionally be coated further with hydrophilic layers.

Materials which may be employed in the formation of the radiopaque marker include, but are not limited to, the noble metals including ruthenium (Ru), rhodium (Rd), palladium (Pd), osmium (Os), iridium (Ir), platinum (Pt), silver (Ag), and gold (Au), tantalum (Ta), rhenium (Re), and so forth, molybdenum, iodine and its salts or compounds, barium and its salts or compounds, bismuth and its salts or compounds, tungsten, and so forth.

Polymeric materials which incorporate radiopaque materials such as barium, may also be employed to form radiopaque marker materials.

In addition to the specific embodiments claimed below, the invention is also directed to other embodiments having any other possible combination of the dependent features claimed below. As such, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on any of claims 1-3, claim 5 may be taken as alternatively dependent from any of claims 1-4, claim 6 may be taken as alternatively dependent from any of claims 1-5; etc.).

The above Examples and disclosure are intended to be illustrative and not exhaustive. These examples and this description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent formed of at least one structural material and having a pattern including a plurality of interconnected circumferential bands including a proximal end band and a distal end band, each of said plurality of said circumferential bands having a distal end and a proximal end, and each of said plurality of circumferential bands formed of a plurality of struts, adjacent struts interconnected by end portions, the end portions having inner turns and outer turns, at least some of the end portions being elongated and other end portions being non-elongated and having a predetermined length, the inner turns of at least one of the non-elongated end portions at the distal end of the proximal end band are substantially unaligned longitudinally with the inner turns of at least one of the non-elongated end portions at the distal end of the proximal end band, the outer turns of at least one of the non-elongated end portions at the distal end of the proximal end band are substantially unaligned longitudinally with the outer turns of at least one of the non-elongated end portions at the distal end of the proximal end band, the inner turns of at least one of the non-elongated end portions of the proximal end of the distal end band are substantially unaligned longitudinally with the inner turns of at least one of the non-elongated end portions at the proximal end of the distal end band, the outer turns of the elongated end portions of the proximal end of the proximal end band are substantially aligned longitudinally with the outer turns of the non-elongated end portions of the proximal end of the proximal end band, and the outer turns of the elongated end portions of the distal end of the distal end band are substantially aligned longitudinally with the outer turns of the non-elongated end portions of the distal end of the distal end band, at least one of said elongated end portions configured to serve as a fiducial marker.

2. The stent of claim 1 wherein the fiducial markers are of the same material as the remainder of the stent.

3. The stent of claim 1 wherein said at least one fiducial marker comprises at least one material which is more radiopaque, has different MR properties, or both than said structural material.

4. The stent of claim 1 wherein said elongated end portions further include at least one void for accepting said at least one fiducial marker.

5. The stent of claim 1 wherein said at least one fiducial marker comprises at least one material which is more radiopaque than said structural material said radiopaque material selected from the group consisting of ruthenium, rhodium, palladium, osmium, iridium, platinum, silver, gold, tantalum, rhenium, molybdenum, iodine and its salts or compounds, barium and its salts or compounds, bismuth and its salts or compounds, tungsten, and mixtures thereof.

6. The stent of claim 1 wherein said fiducial marker comprises at least one material with different MR properties than said structural material.

7. The stent of claim 6 where said material is selected from the group consisting of polychelating and amphiphilic polymers.

8. The stent of claim 1 wherein at least some of the elongated end portions are plated or coated with a radiopaque coating.

9. The stent of claim 1 wherein said fiducial markers comprise at least one material, which is more radiopaque than said structural material, at least one material with different MR properties than said structural material, or both.

10. A stent formed of at least one structural material, said stent having a pattern including at least one first serpentine structure extending about the longitudinal axis, the stent is formed of a plurality struts, said at least one first serpentine structure having a distal end and a proximal end, said at least one first serpentine structure interconnected at said distal end to a proximal end of a second serpentine structure extending about the longitudinal axis of the stent, adjacent struts are interconnected by end portions having inner turns and outer turns at each of said distal end and said proximal end of said at least one serpentine structure, at least some of the end portions being elongated and other end portions being non-elongated and having a predetermined length, the inner turns of at least one of the non-elongated end portions at the distal end of the proximal end band are substantially unaligned longitudinally with the inner turns of at least one of the non-elongated end portions at the distal end of the proximal end band, the outer turns of at least one of the non-elongated end portions at the distal end of the proximal end band are substantially unaligned longitudinally with the outer turns of at least one of the non-elongated end portions at the distal end of the proximal end band, the inner turns of at least one of the non-elongated end portions of the proximal end of the distal end band are substantially unaligned longitudinally with the inner turns of at least one of the non-elongated end portions at the proximal end of the distal end band, the outer turns of the elongated end portions of the proximal end of the proximal end band are substantially aligned longitudinally with the outer turns of the non-elongated end portions of the proximal end of the proximal end band, and the outer turns of the elongated end portions of the distal end of the distal end band are substantially aligned longitudinally with the outer turns of the non-elongated end portions of the distal end of the distal end band, and at least some of the end portions at an end of the stent having extensions which may be configured for serving as fiducial markers for enhanced imaging modality, and having other end portions with no extensions.

11. The stent of claim 10 wherein some of said extensions have at least one fiducial marker which comprises at least one material which is more radiopaque than said structural material, and/or some of said extensions have at least one fiducial marker which comprises at least one material with different MR properties than said structural material.

12. The stent of claim 11 wherein said at least one radiopaque fiducial marker, at least one MR fiducial marker, or both, arc in the form of a wire winding.

13. The stent of claim 10 wherein at least some of the extensions are plated or coated with a radiopaque coating.

14. The stent of claim 10 wherein the at least one serpentine structure extends about the entire circumference of the stent.

15. The stent of claim 10 wherein the at least one serpentine structure extends spirally about the longitudinal axis of the stent.

16. A stent formed of a structural material, said stent having a pattern including a circumferential band having a proximal end and a distal end, said circumferential band formed of a plurality of struts, pairs of adjacent struts interconnected by end portions having inner turns and outer turns, and at the proximal end of the circumferential band at least some of the end portions being elongated as defined by the inner turns and outer turns of said at least some of the end portions and other end portions being non-elongated, said elongated end portions having at least one void, the at least one void within the elongated end portions, said void for accepting at least one fiducial marker, and at the distal end of the circumferential band, the inner turns of at least one of the non-elongated end portions at the distal end of the proximal end band are substantially unaligned longitudinally with the inner turns of at least one of the non-elongated end portions at the distal end of the proximal end band, the outer turns of at least one of the non-elongated end portions at the distal end of the proximal end band are substantially unaligned longitudinally with the outer turns of at least one of the non-elongated end portions at the distal end of the proximal end band, the inner turns of at least one of the non-elongated end portions of the proximal end of the distal end band are substantially unaligned longitudinally with the inner turns of at least one of the non-elongated end portions of the proximal end of the distal end band are substantially aligned longitudinally with the outer turns of the non-elongated end portions of the proximal end of the proximal end band, and the outer turns of the elongated end portions of the distal end of the distal end band are substantially aligned longitudinally with the outer turns of the non-elongated end portions of the distal end of the distal end band.

17. The stent of claim 16 wherein said at least one fiducial marker comprises at least one material which is more radiopaque than said structural material, at least one material with different MR properties than said structural material, or both.

18. The stent of claim 16 wherein said at least one fiducial marker is in the form of a rivet, plug, plating or filling.

19. The stem of claim 16 wherein said inner turns of said elongated end portions having said at least one void are not substantially longitudinally aligned with said inner turns of said other end portions.

20. A method of forming stent having fiducial markers, the method comprising the steps of:
providing a tube of structural material; and
cutting a stent pattern in said structural material, said stent pattern having a plurality of interconnected circumferential bands, each circumferential band having a proximal end and a distal end and formed of a plurality of struts, pairs of adjacent struts interconnected by an end portion, each end portion having an inner turn and outer turn at least some of the end portions being elongated as defined by the inner turn and outer turn of each of said at least some of the end portions and other end portions being non-elongated, the inner turns of at least one of the non-elongated end portions at the distal end of the proximal end band are substantially unaligned longitudinally with the inner turns of at least one of the non-elongated end portions at the distal end of the proximal end band, the outer turns of at least one of the non-elongated end portions at the distal end of the proximal end band are substantially unaligned longitudinally with the outer turns of at least one of the non-elongated end portions at the distal end of the proximal end band, the inner turns of at least one of the non-elongated end portions of the proximal end of the distal end band are substantially unaligned longitudinally with the inner turns of at least one of the non-elongated end portions at the proximal end of the distal end band, the outer turns of the elongated end portions of the proximal end of the proximal end band are substantially aligned longitudinally with the outer turns of the non-elongated end portions of the proximal end of the proximal end band, and the outer turns of the elongated end portions of the distal end of the distal end band are substantially aligned longitudinally with the outer turns of the non-elongated end portions of the distal end of the distal end band, said elongated end portions adapted for enhanced imaging modality portions.

21. The method of claim 20 further comprising the step of cutting at least one void in said elongated end portions.

22. The method of claim 21 further comprising the step of inserting at least one fiducial marker in said void.

23. The method of claim 22 wherein said fiducial marker is in the form of a rivet, plug or filling.

24. The method of claim 22 wherein said at least one fiducial marker comprises at least one material which is more radiopaque than said structural material, at least one material which is more MR visible than said structural material, or both.

25. The method of claim 20 wherein said elongated end portions comprise at least one material which is more radiopaque than said structural material, at least one material which is more MR visible than said structural material, or both.

26. The method of claim 25 wherein some of said elongated end portions have at least one fiducial marker comprising at least one material which is more radiopaque than said structural material and some of said elongated end portions have fiducial markers comprising at least one material which is more MR visible material than said structural material.

27. A method of forming a stent of at least one structural material, said method comprising the steps of:
providing a tube of structural material; and
cutting a pattern in said tube, said pattern including a plurality of interconnected circumferential bands each circumferential band formed of a plurality struts and having a distal end and a proximal end, pairs of adjacent struts interconnected by end portions at each of said proximal end and said distal end of said circumferential band, the end portions having inner turns and outer turns, at least some of the end portions being non-elongated and having a predetermined length, the inner turns of at least one of the non-elongated end portions at the distal end of the proximal end band are substantially unaligned longitudinally with the inner turns of at least one of the non-elongated end portions at the distal end of the proximal end band, the outer turns of at least one of the non-elongated end portions at the distal end of the proximal end band are substantially unaligned longitudinally with the outer turns of at least one of the non-elongated end portions at the distal end of the proximal end band, the inner turns of at least one of the non-elongated end portions of the proximal end of the distal end band are substantially unaligned longitudinally with the inner turns of at least one of the non-elongated end portions at the proximal end of the distal end band, the outer turns of the elongated end portions of the proximal end of the proximal end band are substantially aligned longitudinally with the outer turns of the non-elongated end portions of the proximal end of the proximal end band, and the outer turns of the elongated end portions of the distal end of the distal end band are substantially aligned longitudinally with the outer turns of the non-elongated end portions of the distal end of the distal end band, and at least some of the end portions having extensions for accepting fiducial markers for enhanced imaging modality.

28. The method of claim 27 further comprising the step of winding a wire fiducial marker around said extension.

29. The method of claim 27 further comprising the step of placing a marker band around said extension.

30. The method of claim 28 wherein said wire winding is formed of at least one material which is more radiopaque than said structural material or at least one material which is more MR visible than said structural material.

31. The method of claim 29 wherein said marker band is formed of at least one material, which is more radiopaque than said structural material or at least one material which is more MR visible than said structural material.

32. The method of claim 27 further comprising the steps of winding at least one wire around said extension, said at least one wire comprising at least one material which is more radiopaque than said structural material; and winding at least one wire around said extension, said at least one wire comprising at least one material which is more MR visible than said structural material.

* * * * *